US008700136B2

(12) United States Patent
Rubinstein

(10) Patent No.: US 8,700,136 B2
(45) Date of Patent: Apr. 15, 2014

(54) ACCURATE TIME ANNOTATION OF INTRACARDIAC ECG SIGNALS

(75) Inventor: Vladimir Rubinstein, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 89 days.

(21) Appl. No.: 13/294,412

(22) Filed: Nov. 11, 2011

(65) Prior Publication Data

US 2013/0123652 A1     May 16, 2013

(51) Int. Cl.
*A61B 5/0452*     (2006.01)
(52) U.S. Cl.
USPC .......................................... 600/509; 600/519
(58) Field of Classification Search
USPC .......................................... 600/508, 509, 519
See application file for complete search history.

(56) References Cited

U.S. PATENT DOCUMENTS

| 5,273,049 | A | * | 12/1993 | Steinhaus et al. | ............. | 600/508 |
| 2004/0111021 | A1 | * | 6/2004 | Olson | ........................... | 600/407 |
| 2005/0113703 | A1 | | 5/2005 | Farringdon et al. | | |
| 2006/0167364 | A1 | | 7/2006 | Houben | | |

FOREIGN PATENT DOCUMENTS

WO    WO 2004/093678 A1    11/2004

OTHER PUBLICATIONS

Suppapola et al., "Gaussian Pulse Decomposition: An Intuitive Model of Electrocardiogram Waveforms", Annals of Biomedical Engineering (1997), vol. 25, No. 2, pp. 252-260.
Censi et al., "P-Wave Morphology Assessment by a Gaussian Functions Based Model in Atrial Fibrillation Patients", IEEE Transactions on Biomedical Engineering (Apr. 2007), vol. 54, No. 4, pp. 663-672.
Oezer et al., "A New Approach for Parameterizing the ECG for Sleep Stage Classification", IFMBE Proceedings 25/IV, World Congress on Medical Physics and Biomedical Engineering (Sep. 7-12, 2009), pp. 1044-1047.
Congi et al., "An Automated Measure of P-Wave Duration from Surface ECG Maps", Proceedings of the $25^{th}$ Annual International Conference of the IEEE EMBS (Sep. 17-23, 2003), pp. 78-81.
Hongmin et al., "Detection of Cardiac Signal Characteristic Point Using Log-Domain Wavelet Transform Circuits", Circuits, Systems & Signal Processing (Aug. 13, 2008), pp. 683-698.
Extended European Search Report dated Mar. 28, 2013 issued in EP 12192059.9.

\* cited by examiner

*Primary Examiner* — Eric D. Bertram
(74) *Attorney, Agent, or Firm* — Louis J. Capezzuto

(57) ABSTRACT

A method for analyzing signals, including: sensing a time-varying intracardiac potential signal and finding a fit of the time-varying intracardiac potential signal to a predefined oscillating waveform. The method further includes estimating an annotation time of the signal responsive to the fit.

18 Claims, 6 Drawing Sheets

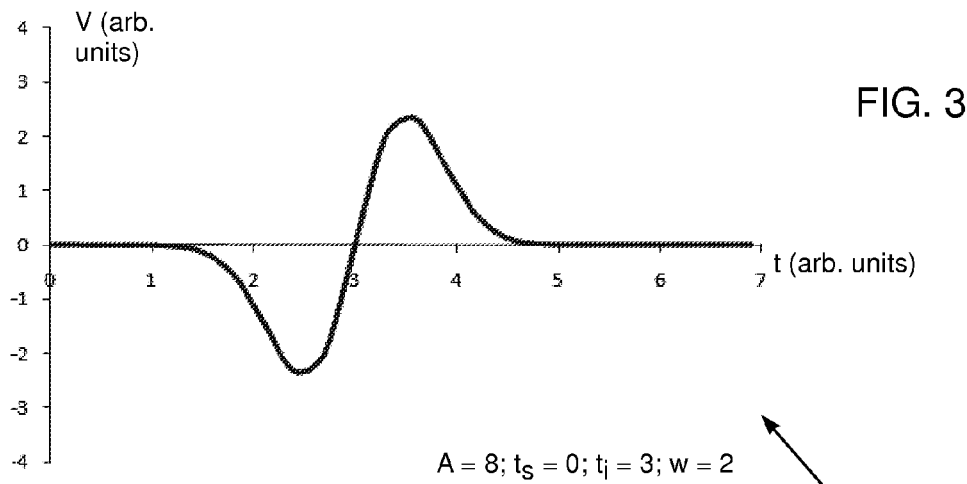
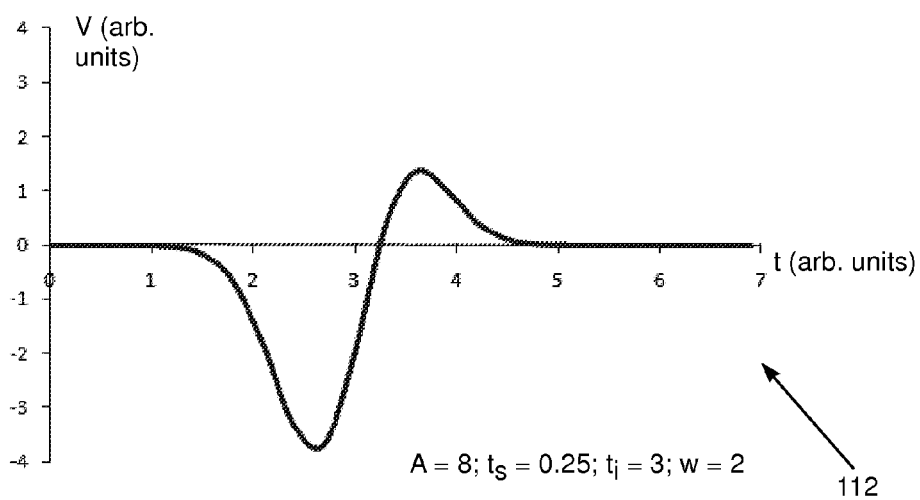
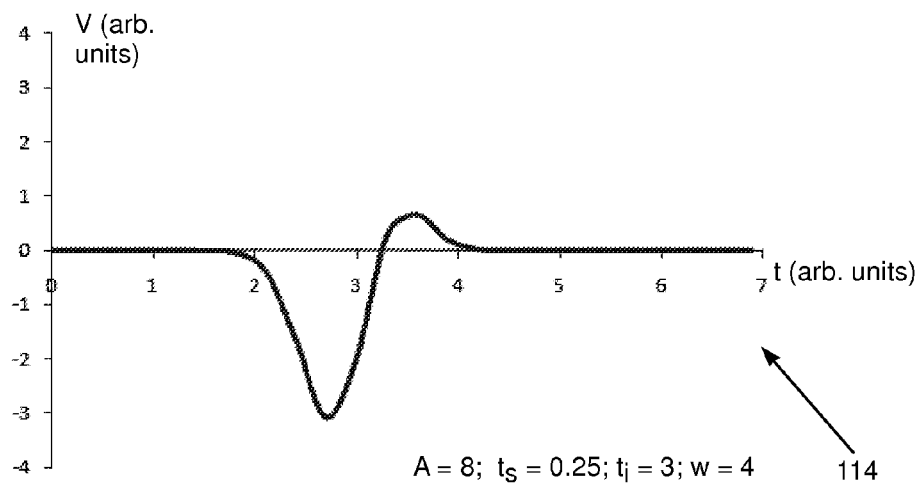
FIG. 3

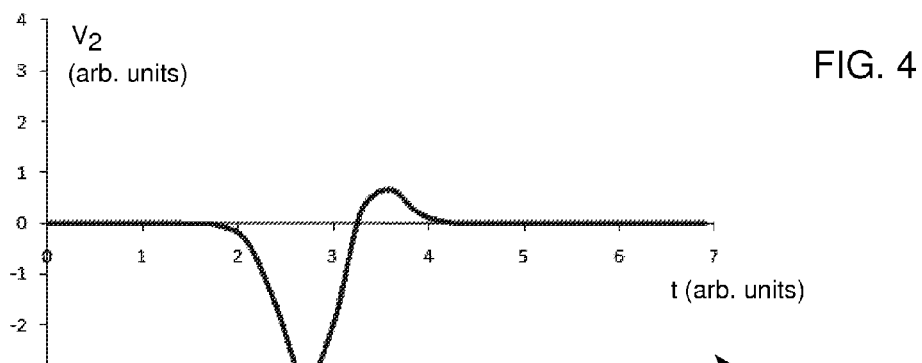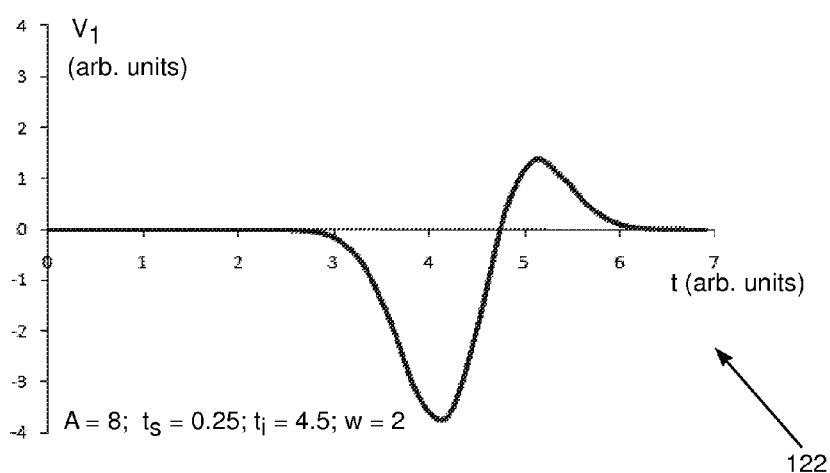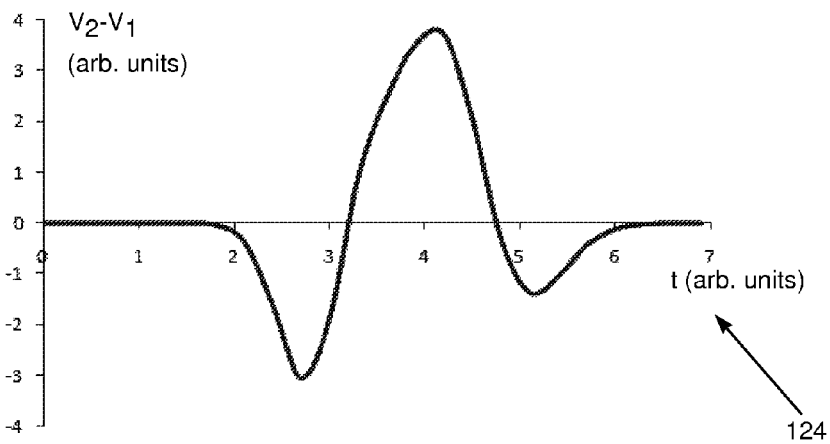
FIG. 4

ACCURATE TIME ANNOTATION OF INTRACARDIAC ECG SIGNALS

FIELD OF THE INVENTION

The present invention relates generally to signal analysis, and specifically to analysis of signals generated during a medical procedure.

BACKGROUND OF THE INVENTION

Electrical signals generated from a patient's body organs, such as the heart, are typically noisy. The signals are typically measured during a medical procedure on the patient, and noise on the signals is usually caused by multiple factors. Some of the factors are artifacts such as movement or changing contact of an electrode with a section of an organ, interference due to other signals being created in proximity to the region being measured, the relatively high impedance of body organs, and inherent changes in the signals being generated.

A process to reduce the effect of noise on signals from body organs is consequently advantageous.

SUMMARY OF THE INVENTION

An embodiment of the present invention provides a method for analyzing signals, including:

sensing a time-varying intracardiac potential signal;

finding a fit of the time-varying intracardiac potential signal to a predefined oscillating waveform; and estimating an annotation time of the signal responsive to the fit.

In a disclosed embodiment the time-varying intracardiac potential signal includes a unipolar signal. Typically, the predefined oscillating waveform includes a single complete oscillation having a single local maximum, a single local minimum, and a single inflection separating the local minimum and maximum.

In an alternative embodiment the predefined oscillating waveform includes a first differential of a Gaussian function. Typically, the first differential is skewed by an asymmetry factor.

In another disclosed embodiment the time-varying intracardiac potential signal includes a bipolar signal. The predefined oscillating waveform may include a difference between a first single complete oscillation and a second single complete oscillation. Typically, the first single complete oscillation includes a first single local maximum, a first single local minimum, and a first inflection separating the first local maximum and minimum, and the second single complete oscillation includes a second single local maximum, a second single local minimum, and a second inflection separating the second local maximum and minimum.

The first single complete oscillation and the second complete oscillation may be separated by a temporal difference. The temporal difference may be a function of a spatial separation of electrodes generating the bipolar signal. Alternatively or additionally, the temporal difference may be a function of an electrode orientation relative to a propagation direction of an activation wave.

In a further disclosed embodiment the predefined oscillating waveform includes a difference between a first Gaussian function first differential and a second Gaussian function first differential. Typically, the first Gaussian function first differential is skewed by a first asymmetry factor and the second Gaussian function first differential is skewed by a second asymmetry factor.

In a yet further disclosed embodiment the time-varying intracardiac potential signal includes three or more unipolar signals having temporal differences therebetween, and wherein a propagation direction of an activation wave is a function of the temporal differences. Typically, respective electrodes having respective positions generate the three or more unipolar signals, and the respective positions may be parameters of the function.

There is further provided, according to an embodiment of the present invention, apparatus for analyzing signals, including:

a sensor configured to sense a time-varying intracardiac potential signal; and a processor configured to:

find a fit of the time-varying intracardiac potential signal to a predefined oscillating waveform, and estimate an annotation time of the signal responsive to the fit.

The present disclosure will be more fully understood from the following detailed description of the embodiments thereof, taken together with the drawings, in which:

BRIEF DESCRIPTION OF THE DRAWINGS

FIGS. 3 and 4 show schematic graphs produced by equations used for fitting to ECG signals, according to embodiments of the present invention;

DETAILED DESCRIPTION OF EMBODIMENTS

Overview

An embodiment of the present invention provides a method for processing a "raw" or filtered intracardiac signal, which may be unipolar or bipolar. Typically the processing comprises fitting the intracardiac signal to a predetermined waveform, and deriving an annotation time of the signal from the fitted signal, rather than from the raw signal.

Typically, a unipolar signal is fitted to an equation representative of a single complete oscillation. A bipolar signal may be fitted to an equation representative of a difference of two single complete oscillations, typically separated by a temporal difference. In some embodiments the single complete oscillation corresponds to a differential of a Gaussian function. An asymmetry factor may be applied to the differential, and in some embodiments the asymmetry factor corresponds to a Gaussian function.

The inventors have found that fitting raw or filtered signals to a predetermined equation, and measuring an annotation time from the fitted signals, reduces variation of the annotation times, as compared to annotation times determined directly from the raw or filtered signals.

System Description

Figure 1:
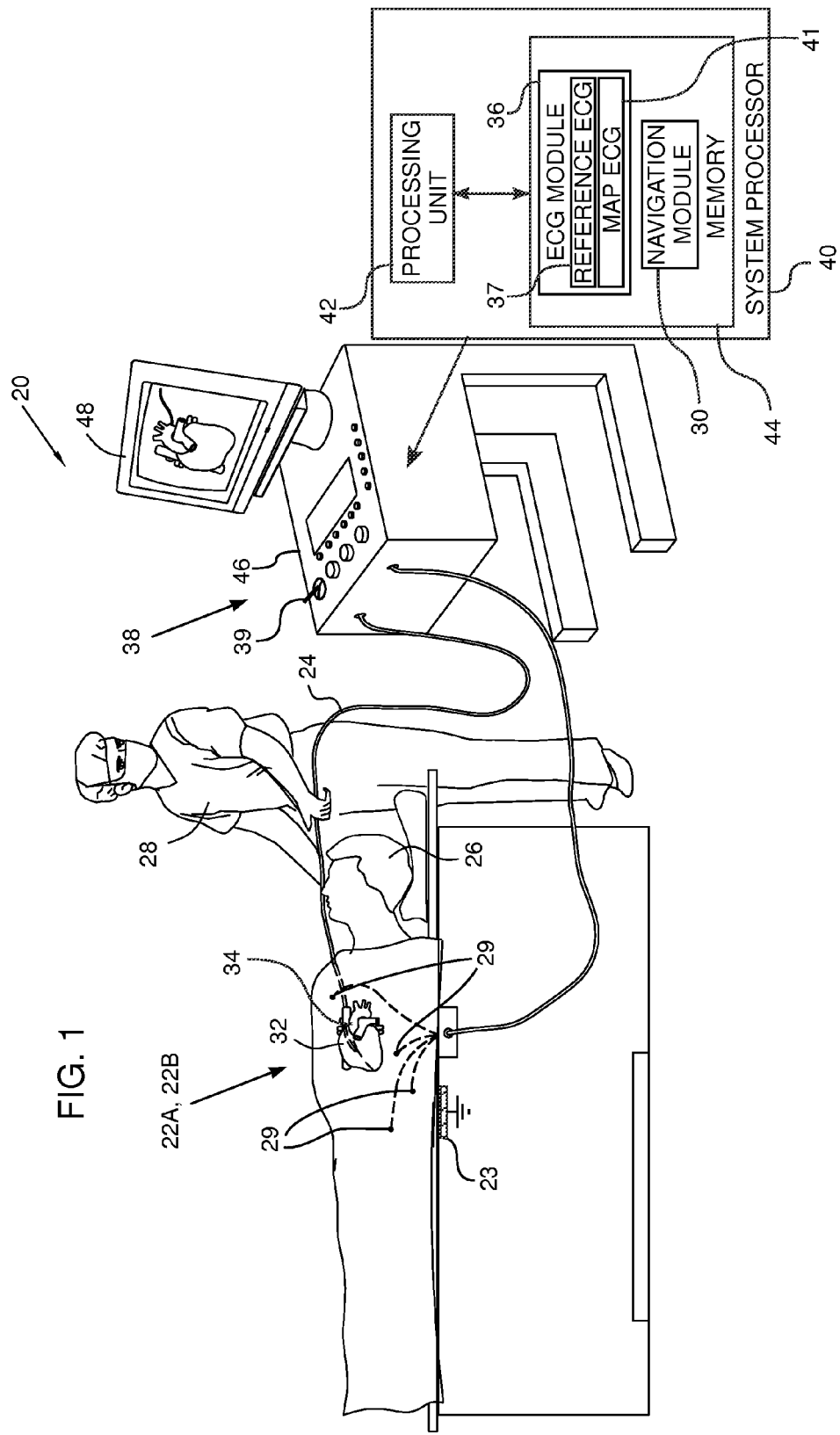
FIG. 1 is a schematic illustration of an electrocardiograph (ECG) analysis system, according to an embodiment of the present invention.

Reference is now made to FIG. 1, which is a schematic illustration of an electrocardiograph (ECG) analysis system 20, according to an embodiment of the present invention. System 20 receives at least one, and typically a plurality of electrical signals from one or more electrodes positioned within an organ of a human patient. Typically, the signals are received from a multiplicity of electrodes placed on one or more probes in the organ. For example, during an invasive procedure on a heart, a first probe with one or more electrodes may be positioned in a reference region of the heart, and used to sense a reference ECG signal from the region. A second probe having multiple electrodes may be used to detect and record other ECG signals from other regions of the heart.

For simplicity and clarity, the following description, except where otherwise stated, assumes an investigative procedure that senses electrical signals from a heart 34, using a single probe 24. Furthermore, a distal end 32 of the probe is assumed to have two substantially similar electrodes 22A, 22B. Electrodes 22A, 22B, may be referred to herein as electrodes 22. Those having ordinary skill in the art will be able to adapt the description for multiple probes having one or more electrodes, as well as for signals produced by organs other than a heart.

Typically, probe 24 comprises a catheter which is inserted into the body of a subject 26 during a mapping procedure performed by a user 28 of system 20. In the description herein user 28 is assumed, by way of example, to be a medical professional. During the procedure subject 26 is assumed to be attached to a grounding electrode 23. In some embodiments, electrodes 29 may be attached to the skin of subject 26, in the region of heart 34.

System 20 may be controlled by a system processor 40, comprising a processing unit 42 communicating with a memory 44. Processor 40 is typically mounted in a console 46, which comprises operating controls 38. Controls 38 typically include a pointing device 39, such as a mouse or a trackball, that professional 28 uses to interact with the processor. The processor uses software, including a probe navigation module 30 and an ECG module 36, stored in memory 44, to operate system 20. ECG module 36 comprises a reference ECG sub-module 37 and a map ECG sub-module 41, whose functions are described below. Results of the operations performed by processor 40 are presented to the professional on a display 48, which typically presents a graphic user interface to the operator, a visual representation of the ECG signals sensed by electrodes 22, and/or an image of heart 34 while it is being investigated. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive electrical signals from electrodes 22. The module may also be coupled to receive signals from one or more of electrodes 29. The ECG module is configured to analyze the signals and may present the results of the analysis in a standard ECG format, typically a graphical representation moving with time, on display 48.

Probe navigation module 30 tracks sections of probe 24 while the probe is within subject 26. The navigation module typically tracks both the location and orientation of distal end 32 of probe 24, within the heart of subject 26. In some embodiments module 30 tracks other sections of the probe. The navigation module may use any method for tracking probes known in the art. For example, module 30 may operate magnetic field transmitters in the vicinity of the subject, so that magnetic fields from the transmitters interact with tracking coils located in sections of the probe being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, navigation module 30 may track probe 24 by measuring impedances between electrode 23, electrodes 29 and electrodes 22, as well as the impedances to other electrodes which may be located on the probe. (In this case electrodes 22 and/or electrodes 29 may provide both ECG and tracking signals.) The Carto3® system produced by Biosense Webster uses both magnetic field transmitters and impedance measurements for tracking.

Figure 2:
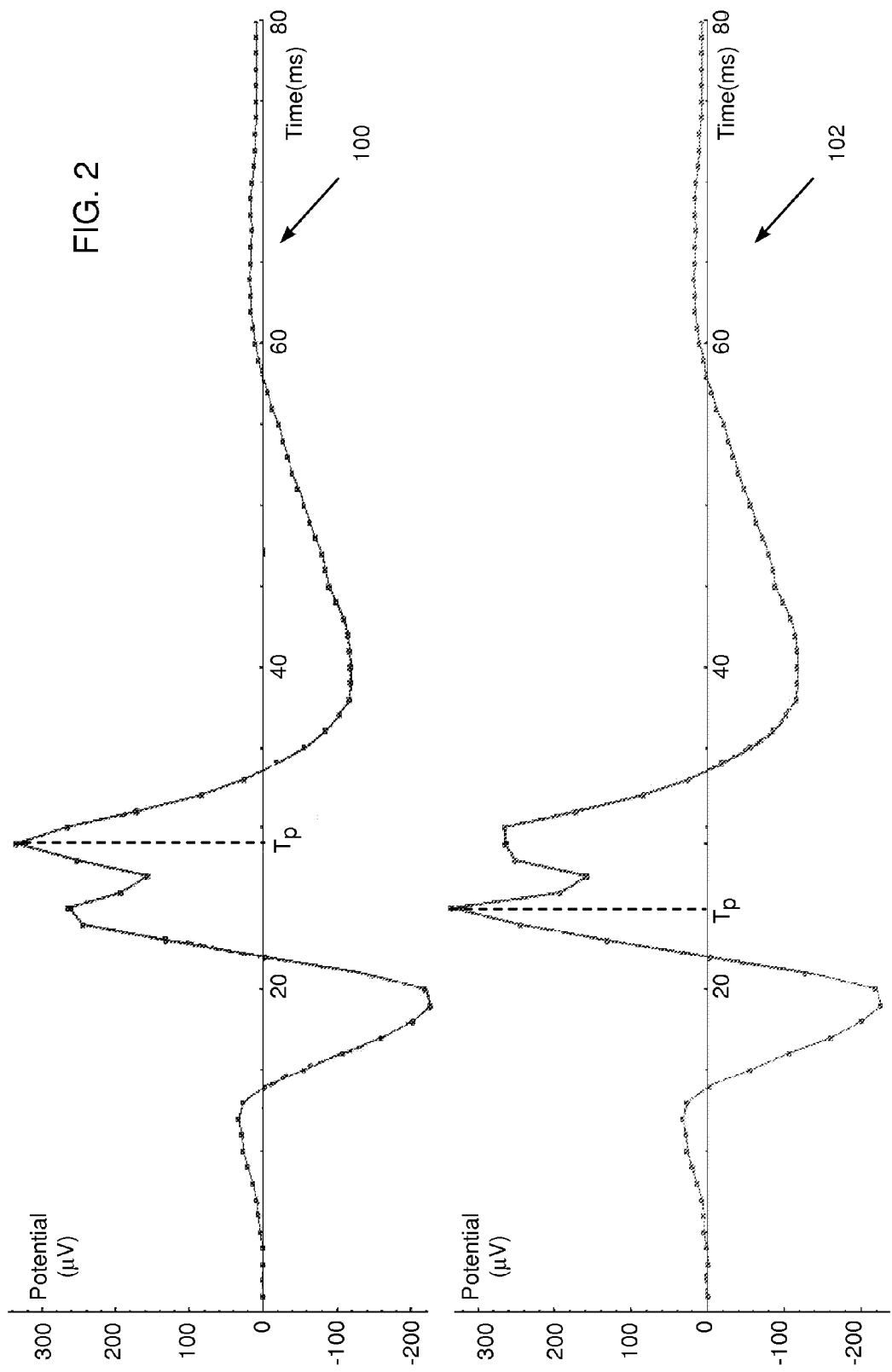
FIG. 2 shows schematic graphs of typical ECG signals processed by the ECG analysis system, according to an embodiment of the present invention.

FIG. 2 shows schematic graphs of typical ECG signals processed by system 20, according to an embodiment of the present invention. Graphs 100, 102 show exemplary potential vs. time plots of "raw" (i.e., unprocessed) bipolar intracardiac ECG signals. The signals are assumed to be derived from the potential differences between electrode 22A and electrode 22B while the electrodes contact a wall of the heart. As is known in the art, intracardiac ECG signals are noisy, the noise typically being generated by a number of factors, such as line radiation, the proximity of other electrical equipment, and other electrical sources derived from patient 26, such as patient muscular contraction (apart from heart muscles). The noise typically causes problems in making quantitative measurements of annotation times from the raw signals.

For example, an annotation time, $T_p$, comprising the time of the "R" peak of the signal, may be required, the time being measured from the onset of the signal. Graph 100 illustrates that $T_p$ is measured to be approximately 30 ms, whereas graph 102 illustrates that $T_p$ is measured to be approximately 25 ms. As is illustrated in the graphs, the measured value of $T_p$ varies.

As stated above, graphs 100, 102 illustrate bipolar graphs generated by difference signals between electrode 22A and 22B. The signal on each electrode 22A or 22B, when measured relative to a common reference electrode, is a unipolar signal, so that the bipolar signal may be considered as a difference between two unipolar signals. The reference electrode may be any convenient electrode, such as grounding electrode 23, and/or one or more of skin electrodes 29, and/or one or more other electrodes in contact with the heart.

FIGS. 3 and 4 show schematic graphs produced by equations used for fitting to ECG signals, according to embodiments of the present invention. Embodiments of the present invention fit a predetermined equation to signals such as the ECG signals illustrated in FIG. 2. The equation corresponds to a predetermined oscillating waveform, typically a waveform that is in the form of a single complete oscillation, i.e., a waveform that has beginning and end points that have a substantially zero signal level, and that encompasses all the electrical activity between the two points. Typically, the graph of a single complete oscillation has a single local minimum and a single local maximum. The local maximum and local minimum may be separated by a single inflection.

In some embodiments, and as exemplified herein, the predetermined equation fitted to the signals is derived from the first differential of a Gaussian function, skewed by an asymmetry factor.

Thus, for unipolar ECG signals received from electrodes 22A or 22B, processor 40 fits an equation having the general form given by equation (1) below to the signals:

$$V_{unipolar}(t) = A \frac{((t-t_i)-t_s)}{e^{w(t-t_i)^2}} \quad (1)$$

where $V_{unipolar}(t)$ represents the varying unipolar potential signal measured at the electrode at a time t;

$t_i$ is a temporal displacement of the signal, with respect to the time t=0. $t_i$ corresponds to the time when an activation wave passes through the electrode position;

A is an amplitude of the signal;

$t_s$ is a parameter defining an asymmetry of the signal; and w is a parameter defining a width of the signal.

Inspection of equation (1) shows that the asymmetry factor provided by the equation corresponds to a Gaussian function. Thus, equation (1) sums a Gaussian function and a first differential of a Gaussian function.

In the description below, parameters $t_{i1}$, A1, $t_{s1}$, and $w_1$, are also referred to collectively as the unipolar fitting parameters of equation (1).

Graphs 110, 112, and 114 (FIG. 3) illustrate the effects of values of parameters $t_s$ and w on the waveform generated by equation (1). For simplicity, the units of the ordinate and the abscissa of each graph are assumed to be arbitrary. As shown by graph 110, for $t_s$=0, the graph has two-fold symmetry, having a center of symmetry at (3, 0). (In other words, under a rotation of 180° in the plane of the graph the graph transforms into itself.) Graph 112 shows that for a positive value of $t_s$=3, the graph becomes asymmetric. The asymmetry increases with increasing $t_s$.

As shown by graph 114, the value of w changes the overall width of the graph, so that increasing the value of w reduces the width.

If the ECG signal is a bipolar signal, it may be assumed to be generated by the difference between a unipolar signal $V_{unipolar}(t)_1$ on electrode 22A and a unipolar signal $V_{unipolar}(t)_2$ on electrode 22B. For bipolar signals such as these the processor fits an equation (2), derived from equation (1), to the signal:

$$V_{bipolar}(t) = \qquad (2)$$
$$V_{unipolar}(t)_2 - V_{unipolar}(t)_1 = A_2 \frac{((t - t_{i2}) - t_{s2})}{e^{w_2(t-t_{i2})^2}} - A_1 \frac{((t - t_{i1}) - t_{s1})}{e^{w_1(t-t_{i1})^2}}$$

where $V_{bipolar}(t)$ represents the varying bipolar potential signal measured at the electrode at a time t;

$V_{unipolar}(t)_1$, $V_{unipolar}(t)_2$, also termed $V_1$ and $V_2$, are as defined above for equation (1);

$t_{i1}$, $t_{i2}$ are temporal displacements of $V_1$, $V_2$;

A1, A2 are amplitudes of $V_1$, $V_2$;

$t_{s1}$, $t_{s2}$ define asymmetries of $V_1$, $V_2$; and $w_1$, $w_2$ define widths of $V_1$, $V_2$.

For a bipolar signal there is a temporal difference, $\Delta t_i = t_{i1} - t_{i2}$, equal to a difference between the temporal displacements of the two unipolar signals $V_{unipolar}(t)_1$ and $V_{unipolar}(t)_2$. The temporal difference between the two unipolar signals is typically a function of the spatial separation of the two electrodes generating the bipolar signal, and of an electrode orientation relative to a propagation direction of the activation wave. Thus, in the case of two electrodes, at least a component of the propagation direction of the activation wave may be determined from the temporal difference of the unipolar signals. It will be appreciated that for more than two electrodes, the temporal differences between the respective unipolar signals detected by the more than two electrodes, as well as the positions of the electrodes, typically allow multiple components of the propagation direction to be found. From the multiple components, the propagation direction (not just a component) of the activation wave may be estimated.

In the description below, parameters $t_{i1}$, $t_{i2}$, A1, A2, $t_{s1}$, $t_{s2}$, and $w_1$, $w_2$ are also referred to collectively as the bipolar fitting parameters of equation (2).

Graphs 120, 122, and 124 (FIG. 4) illustrate the application of equation (2). Graphs 120 and 122 are graphs of two unipolar equations of voltage vs. time, respectively having temporal displacements (in arbitrary units) of t=3 and t=4.5, and widths of 4 and 2. Graph 124 is the graph of the difference of the two expressions, illustrating a bipolar voltage vs. time function having a temporal difference of $\Delta t=4.5-3=1.5$.

Generated intracardiac unipolar and bipolar signals depend, inter alia, on the positions of the electrodes used to measure the signals. The generated signals also depend on the condition of the heart being measured, i.e., whether the heart is functioning in a healthy or unhealthy manner.

If a heart is unhealthy because of a specific defect, it also produces standard intracardiac signals, different from those of a healthy heart (similar differences may be used in diagnoses using skin ECG signals, i.e., body surface signals). In the case of a specific defect, the unhealthy heart generates standard deficient unipolar or bipolar signals, the deficiency in the signals being caused by the respective heart defect.

Figure 5:
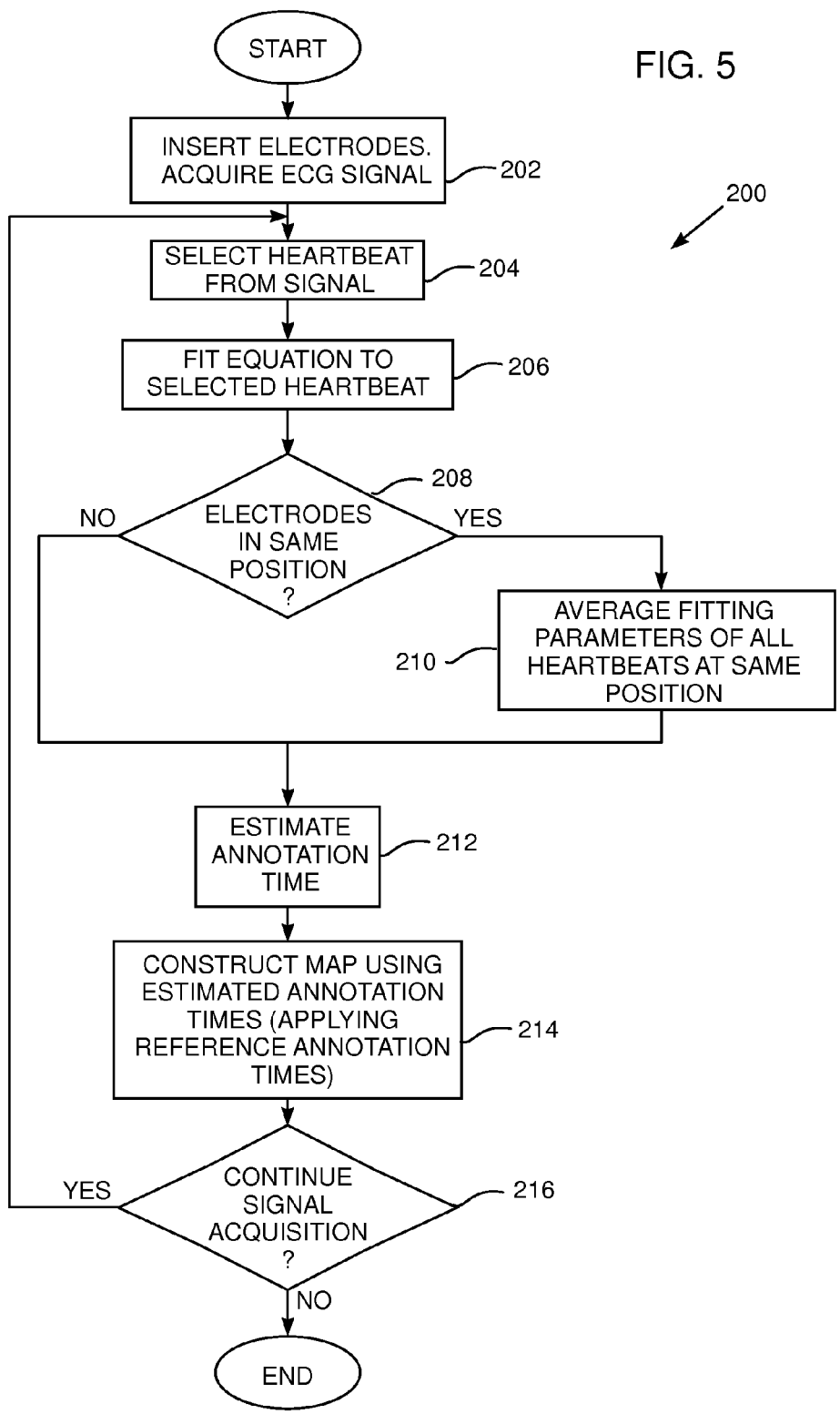
FIG. 5 is a flowchart showing steps in analyzing intracardiac signals, according to an embodiment of the present invention.

FIG. 5 is a flowchart 200 showing steps performed by processor 40 in analyzing intracardiac signals, according to an embodiment of the present invention. In the following description the signals are assumed to comprise bipolar signals. Those having ordinary skill in the art will be able to adapt the description, mutatis mutandis, for unipolar signals.

In an initial step 202, professional 28 inserts probe 24 into heart 34, so that electrodes 22A and 22B are in contact with a section of the heart wall. Processor 40 acquires intracardiac bipolar ECG signals from the electrodes, each ECG signal comprising ordered pairs of potentials V and times t: $\{(V,t)\}$.

In a heartbeat selection step 204, one complete heartbeat is selected. Thus, if the duration of the selected heartbeat is T, and the acquisition in step 202 is performed at a sample rate SampleRate, there are approximately T/SampleRate samples of bipolar signals in the selected heartbeat.

In an analysis step 206, the processor fits equation (2) to the selected heartbeat to derive a set of values of the fitting parameters of equation (2) that give a best fit to the selected heartbeat.

In a comparison step 208, the processor uses navigation module 30 to check if electrodes 22A and 22B are in the same position with respect to the heart. If the comparison returns a positive result, so that the electrodes are in the same position, then in an averaging step 210 the processor averages the fitting parameters for all the heartbeats at the position, to generate a set of averaged fitting parameters. The flowchart then continues at an annotation time step 212.

If the comparison returns a negative result, so that the electrodes have moved, then no averaging is performed, and the flowchart continues directly to step 212.

In annotation time step 212, the fitting parameters derived either in step 210 (if averaging has occurred) or in step 206 (if there has been no averaging) are used to estimate an annotation time. The annotation time is a reference time of occurrence of a characteristic of the ECG signal. The annotation time may be defined with respect to the body surface ECG, or with respect to an intracardiac reference ECG, for example from a catheter placed in the coronary sinus. Typical signal characteristics used to define the reference annotation time include, but are not limited to, the time at which the R-peak maximum of the QRS complex occurs, the time at which the minimum derivative of the QRS complex occurs, the time at which a center of energy of the complete signal occurs, or the time at which a first indication of the complete signal occurs.

The reference annotation time is typically dependent on the position in the heart at which the signal is measured. Definitions for the reference annotation times and their values are stored in reference ECG sub-module 37.

In a map building step 214, the processor constructs a point of an electro-anatomical map of heart 34. To construct the map point, the processor incorporates the difference of annotation times estimated in step 212 and the relevant reference annotation time (stored in sub-module 37) into a map of the heart (using navigation module 30) (FIG. 1). Sub-module 41 is also used in this step.

The repetition of steps 202-214 is indicated by a continuation condition 216 returning a positive result. If condition 216 returns a negative result, typically by professional 28 deciding to stop the mapping procedure of step 214, the flowchart ends.

As stated above, steps 202-214 can be typically performed for different situations comprising different positions of the electrodes in healthy hearts and in unhealthy hearts with known defects.

Figure 6:
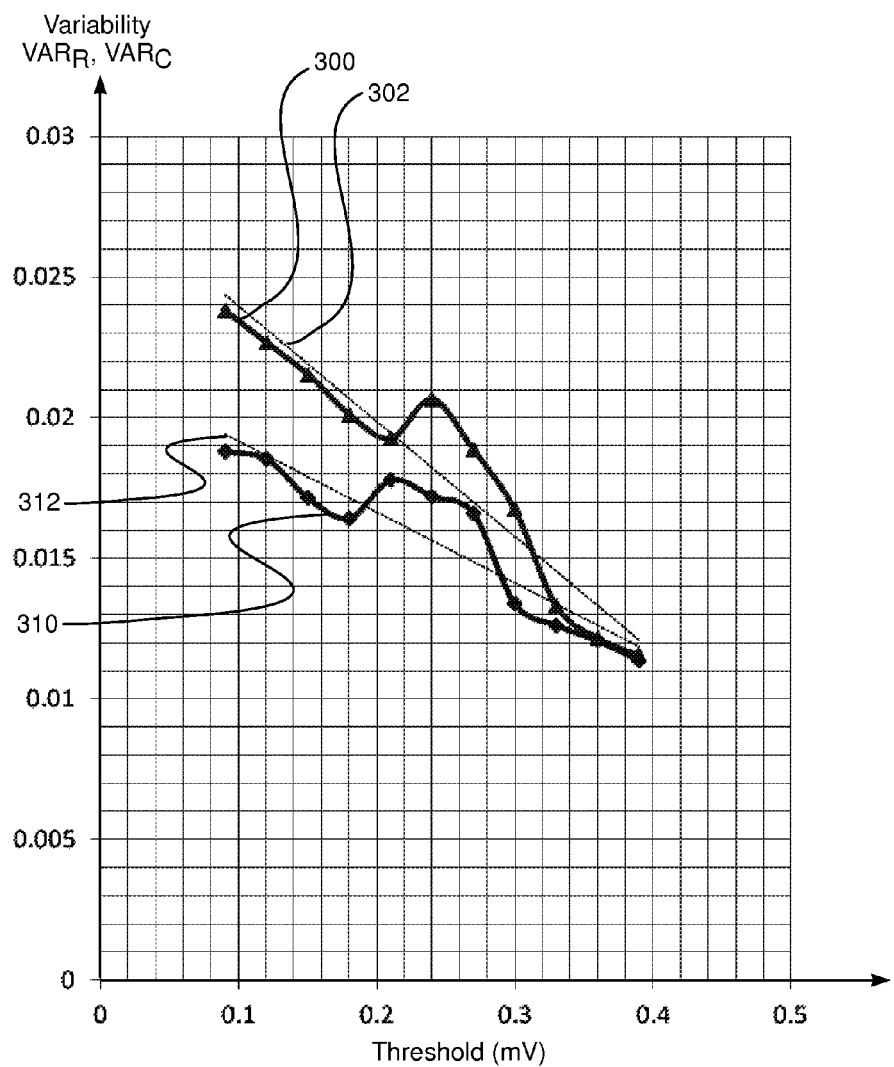
FIG. 6 shows schematic graphs illustrating results obtained by the system of FIG. 1, according to an embodiment of the present invention.

FIG. 6 shows schematic graphs illustrating the results of applying the methods described above, according to an embodiment of the present invention. Intracardiac ECG signals were recorded from several different cases, to create a data pool. Approximately 5,900 heartbeats were extracted from the data pool. All heartbeats were organized into eleven groups, each group containing a heartbeat with an amplitude less than a pre-determined threshold.

The threshold is a measure of the noise of the signal, so that signals having lower thresholds have higher noise levels. For each heartbeat in a specific group the time of occurrence $t_{Rk}$ of the R-peak maximum, and the time of occurrence $t_{Ck}$ of the passing of the activation wave, were estimated. k is an index representing a number of the heartbeat being measured. $t_{Ck}$ was estimated using a fitting analysis similar to that described for flowchart 200, herein also referred to as a fit annotation method. The method for estimating $t_{Rk}$ is also referred to herein as the maximum annotation method.

Within each group, the following differences in times were calculated:

$$\Delta t_R = t_{Rk} - t_{R(k-1)}$$

$$\Delta t_C = t_{Ck} - t_{C(k-1)} \quad (3)$$

From equations (3) the following variability coefficients were calculated:

$$VAR_R = \frac{\sigma(\Delta t_R)}{M(\Delta t_R)} \quad (4)$$

$$VAR_C = \frac{\sigma(\Delta t_C)}{M(\Delta t_C)}$$

where $\sigma(\Delta t)$ is a standard deviation of all $\Delta t$ values, and $M(\Delta t)$ is a mean of all the $\Delta t$ values.

The expressions of equations (4) give a measure of the variability of the annotation times by the maximum annotation method or by the fit annotation method of heartbeats within a given group.

A graph 300 plots the variability $VAR_R$ vs. the threshold of a group, and a graph 302 is a linear regression of graph 300. A graph 310 plots the variability $VAR_C$ vs. the threshold of a group, and a graph 312 is a linear regression of graph 310. By comparison of the two sets of graphs, it is apparent that for low values of the threshold, i.e., for signals with high noise values, the variability of the signals processed according to methods described herein, i.e., using the fit annotation method, is less than the variability of signals that have not been processed with these methods.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for analyzing signals, comprising:
   sensing a time-varying intracardiac potential signal;
   finding a fit of the time-varying intracardiac potential signal to a predefined oscillating waveform; and
   estimating a reference time of occurrence of a characteristic of the signal responsive to the fit,
   wherein the time-varying intracardiac potential signal comprises a bipolar signal, and
   the predefined oscillating waveform comprises a difference between a first single complete oscillation and a second single complete oscillation.

2. The method according to claim 1, wherein the first single complete oscillation comprises a first single local maximum, a first single local minimum, and a first inflection separating the first local maximum and minimum, and wherein the second single complete oscillation comprises a second single local maximum, a second single local minimum, and a second inflection separating the second local maximum and minimum.

3. The method according to claim 1, wherein the first single complete oscillation and the second complete oscillation are separated by a temporal difference.

4. The method according to claim 3, wherein the temporal difference is a function of a spatial separation of electrodes generating the bipolar signal.

5. The method according to claim 3, wherein the temporal difference is a function of an electrode orientation relative to a propagation direction of an activation wave.

6. A method for analyzing signals, comprising:
   sensing a time-varying intracardiac potential signal;
   finding a fit of the time-varying intracardiac potential signal to a predefined oscillating waveform; and
   estimating a reference time of occurrence of a characteristic of the signal responsive to the fit,
   wherein the time-varying intracardiac potential signal comprises a bipolar signal, and
   the predefined oscillating waveform comprises a difference between a first Gaussian function first differential and a second Gaussian function first differential.

7. The method according to claim 6, wherein the first Gaussian function first differential is skewed by a first asymmetry factor and the second Gaussian function first differential is skewed by a second asymmetry factor.

8. A method for analyzing signals, comprising:
   sensing a time-varying intracardiac potential signal;
   finding a fit of the time-varying intracardiac potential signal to a predefined oscillating waveform; and
   estimating a reference time of occurrence of a characteristic of the signal responsive to the fit,
   wherein the time-varying intracardiac potential signal comprises three or more unipolar signals having temporal differences therebetween, and wherein a propagation direction of an activation wave is a function of the temporal differences.

9. The method according to claim 8, wherein respective electrodes having respective positions generate the three or more unipolar signals, and wherein the respective positions comprise parameters of the function.

10. Apparatus for analyzing signals, comprising:
a sensor configured to sense a time-varying intracardiac potential signal; and
a processor configured to:
find a fit of the time-varying intracardiac potential signal to a predefined oscillating waveform, and estimate a reference times of occurrence of a characteristic of the signal responsive to the fit,
wherein the time-varying intracardiac potential signal comprises a bipolar signal, and
the predefined oscillating waveform comprises a difference between a first single complete oscillation and a second single complete oscillation.

11. The apparatus according to claim 10, wherein the first single complete oscillation comprises a first single local maximum, a first single local minimum, and a first inflection separating the first local maximum and minimum, and wherein the second single complete oscillation comprises a second single local maximum, a second single local minimum, and a second inflection separating the second local maximum and minimum.

12. The apparatus according to claim 10, wherein the first single complete oscillation and the second complete oscillation are separated by a temporal difference.

13. The apparatus according to claim 12, wherein the temporal difference is a function of a spatial separation of electrodes generating the bipolar signal.

14. The apparatus according to claim 12, wherein the temporal difference is a function of an electrode orientation relative to a propagation direction of an activation wave.

15. An apparatus for analyzing signals, comprising:
a sensor configured to sense a time-varying intracardiac potential signal; and
a processor configured to:
find a fit of the time-varying intracardiac potential signal to a predefined oscillating waveform, and estimate a reference times of occurrence of a characteristic of the signal responsive to the fit,
wherein the time-varying intracardiac potential signal comprises a bipolar signal, and
wherein the predefined oscillating waveform comprises a difference between a first Gaussian function first differential and a second Gaussian function first differential.

16. The apparatus according to claim 15, wherein the first Gaussian function first differential is skewed by a first asymmetry factor and the second Gaussian function first differential is skewed by a second asymmetry factor.

17. An apparatus for analyzing signals, comprising:
a sensor configured to sense a time-varying intracardiac potential signal; and
a processor configured to:
find a fit of the time-varying intracardiac potential signal to a predefined oscillating waveform, and estimate a reference times of occurrence of a characteristic of the signal responsive to the fit,
wherein the time-varying intracardiac potential signal comprises three or more unipolar signals having temporal differences therebetween, and wherein a propagation direction of an activation wave is a function of the temporal differences.

18. The apparatus according to claim 17, wherein respective electrodes having respective positions generate the three or more unipolar signals, and wherein the respective positions comprise parameters of the function.

* * * * *